United States Patent [19]

Schmid

[11] Patent Number: 4,816,581
[45] Date of Patent: Mar. 28, 1989

[54] 4-(PHENYLTHIO OR PHENYLSULFONYL) AZETIDINONES AND PROCESS OF MANUFACTURE

[75] Inventor: Gérard Schmid, Kienberg, Switzerland

[73] Assignee: Hoffman-La Roche Inc., Nutley, N.J.

[21] Appl. No.: 104,580

[22] Filed: Sep. 28, 1987

Related U.S. Application Data

[63] Continuation of Ser. No. 786,449, Oct. 11, 1985, abandoned.

[30] Foreign Application Priority Data

Oct. 18, 1984 [CH] Switzerland .................. 4995/84

[51] Int. Cl.[4] .............. C07D 205/08; C07F 7/18; C07B 53/00; C07B 43/06
[52] U.S. Cl. ..................... 540/359; 540/360
[58] Field of Search ................. 540/359, 360

[56] References Cited

PUBLICATIONS

K. Hirai, Chem Pharm Bull 21, 1090 (1973).
Favara, Tet. Letters 23, 3105 (1982).
Moriconi, Tet. Letters 1968, 1435.

*Primary Examiner*—Mark L. Berd
*Attorney, Agent, or Firm*—Jon S. Saxe; Bernard S. Leon; George W. Johnston

[57] ABSTRACT

The novel compounds of the formula

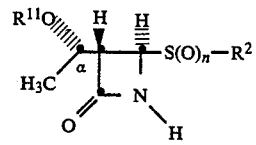

wherein $R^{11}$ signifies hydrogen, acyl or tri(lower alkyl)silyl, $R^2$ signifies a phenyl group which is substituted in the o- and/or the p-position by halogen, lower alkyl, lower alkylthio or lower alkoxy and n signifies the number 0 or 2, and mixtures thereof with the corresponding optical antipodes are valuable intermediates for the manufacture of antimicrobially active penems and carbapenems which have as a common structural element a (R)-1-hydroxyethyl group in the 6-position. They can be manufactured by reacting a compound of the formula

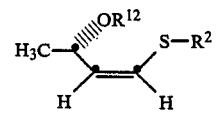

wherein $R^{12}$ signifies acyl, tri(lower alkyl)silyl or a group of the formula —$BR^3R^4$ and $R^3$ and $R^4$ have the same significance and each signify a branched-open chain, cyclic or bicyclic hydrocarbon residue with 5-10 carbon atoms or together signify an open chain or cyclic hydrocarbon residue with 5-10 carbon atoms and two free valencies and $R^2$ has the above significance, or a mixture thereof with the corresponding optical antipode with chlorosulphonyl isocyanate and, if desired, S-oxidizing a resulting compound of formula I in which n signifies the number O and, previously or subsequently, cleaving off an acyl or tri(lower alkyl)silyl group which may be present.

5 Claims, No Drawings

4-(PHENYLTHIO OR PHENYLSULFONYL) AZETIDINONES AND PROCESS OF MANUFACTURE

This application is a continuation, of application Ser. No. 786,449, filed Oct. 11, 1985 now abandoned.

BACKGROUND OF THE INVENTION

This invention relates to beta-lactam intermediates.

SUMMARY OF THE INVENTION

The present invention is concerned with sterically uniform 2-azetidinones of the formula

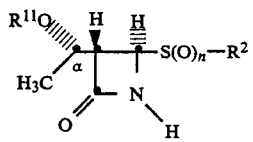

wherein $R^{11}$ signifies hydrogen, acyl or tri(lower alkyl)-silyl, $R^2$ signifies a phenyl group which is substituted in the o- and/or the p-position by halogen, lower alkyl, lower alkylthio or lower alkoxy and n signifies the number 0 or 2, and mixtures thereof with the corresponding optical antipodes (including the racemate).

These novel substances are valuable intermediates for the manufacture of antimicrobially active penems and carbapenems which have as a common structural element a (R)-1-hydroxyethyl group in the 6-position.

The present invention is concerned with the above compounds of formula I and mixtures thereof with the corresponding optical antipodes per se, intermediates and a process for their manufacture and their use for the manufacture of the aforementioned penems and carbapenems.

DETAILED DESCRIPTION OF THE INVENTION

The present invention is concerned with optically active beta-lactam intermediates of the formula

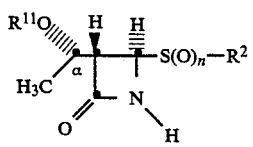

wherein $R^{11}$ is hydrogen, acyl or tri(lower alkyl)silyl; $R^2$ is phenyl which is substituted in the o- and/or the p-position by halogen, lower alkyl, lower alkylthio or lower alkoxy; and n is the integer 0 or 2; and mixtures thereof with the corresponding optical antipodes.

The term "lower" denotes residues and compounds having a maximum of 7, preferably a maximum of 4, carbon atoms. The term "alkyl", taken alone or in combinations (such as alkylthio, alkoxy and the like) denotes straight-chain or branched, saturated hydrocarbon residues of 1 to 7 carbon atoms such as methyl and t-butyl. The term "halogen" denotes the four forms fluorine, chlorine, bromine and iodine.

The term "lower alkanoyl" denotes moieties derived from alkanecarboxylic acid moieties (e.g., formyl, acetyl, propionyl, etc.).

The term "alkoxy" denotes alkyl groups having an oxygen atom (e.g., methoxy ethoxy, isopropoxy, etc.).

The term "acyl" preferably denotes lower alkanoyl groups such as acetyl and the like, lower alkoxycarbonyl phenyl-lower alkanoyl group unsubstituted or optionally substituted on the phenyl ring by halogen, lower alkyl or lower alkoxy.

The term "branched-open chain, cyclic or bicyclic hydrocarbon residue with 5-10 carbon atoms" used below denotes a) branched, open chain, saturated hydrocarbon residues with 5-10, preferably 5-7, carbon atoms such as isoamyl, b) cyclic, saturated hydrocarbon residues with 5-10 carbon atoms, whereby the carbocycle preferably contains 5-7 carbon atoms and the remaining carbon atoms can be preeent in the form of lower alkyl substituents, such as cyclopentyl, cyclohexyl, 2-methylcyclohexyl and the like, and c) saturated, bicyclic hydrocarbon residues, whereby preferably 7-9 carbon atoms are components of the bicycle and the remaining carbon atoms can be attached to the bicycle in the form of lower alkyl groups, such as e.g. the 3-pinanyl residue.

The term "open chain or cyclic hydrocarbon residue with 5-10 carbon atoms and two free valencies" used below denotes a) saturated, open chain hydrocarbon residues, whereby preferably 3-4 carbon atoms are situated between the two carbon atoms with the free valencies and the remaining carbon atoms can be attached to the open chain residue in the form of lower alkyl groups, such as e.g. the 2,4-dimethylpentamethylene residue, and b) saturated, cyclic hydrocarbon residues, whereby preferably 6-8 carbon atoms are components of a carbocycle with two free valencies and the remaining carbon atoms can be attached to the carbocycle in the form of lower alkyl groups, such as e.g. the cyclooctane-1,5-diyl residue.

In the pictorial representations of the compounds of this application, a solid tapering line indicates a substituent which is in the beta-orientation (above the plane of the molecule) and a series of parallel lines indicates a substituent which is in the alpha-orientation (below the plane of the molecule).

The symbol $R^{11}$ preferably signifies hydrogen or t-butyldimethylsilyl. The symbol $R^2$ preferably signifies a phenyl group which is substituted in the p-position by halogen or lower alkoxy. The symbol n preferably signifies the number 0.

preferred representatives of the class of substance in accordance with the invention are:
(αS,3S,4R)-3-[1-(t-Butyldimethylsilyloxy)ethyl]-4-[(p-chlorophenyl)thio]-2-azetidinone,
(αS,3S,4R)-3-[1-(t-butyldimethylsilyloxy)ethyl]-4-[(p-methoxyphenyl)thio]-2-azetidinone,
(αS,3S,4R)-4-[(p-chlorophenyl)thio]-3-(1-hydroxyethyl)-2-azetidinone and
(αS,3S,4R)-3-(1-hydroxyethyl)-4-[(p-methoxyphenyl)-thio]-2-azetidinone.

The compounds of formula I and mixtures thereof with the corresponding antipodes can be manufactured in accordance with the invention by reacting a compound of the formula

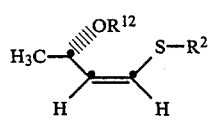

wherein $R^{12}$ is acyl, tri(lower alkyl)silyl or a group of the formula and —$BR^3R^4$ and $R^3$ and $R^4$ have the same significance and each signify a branched-open chain, cyclic or bicyclic hydrocarbon residue with 5-10 carbon atoms or together signify an open chain or cyclic hydrocarbon residue with 5-10 oarbon atoms and two tree valencies and R has the above significance, or a miXture thereof With the corresponding optical antipode with chlorosulphonyl isocyanate and, if desired, S-oxidizing a resulting compound of formula I in which n signifies the number 0 and, previously or subsequently. cleaving off an acyl or tri(lower alkyl)silyl group which may be present.

The reaction of a compound of formula IIa with chlorosulphonyl isocyanate is a cycloaddition which is known per se and which is familiar to any person skilled in the art. The reaction is conveniently carried out in an inert organic solvent, with a halogenated, lower hydrocarbon being preferably used. Methylene chloride is a particularly preferred solvent. In the course of the usual working-up of the reaction mixture not only the chlorosulphonyl group, but also a group of the formula —$BR^3R^4$ which may be present is cleaved off, as these groups are very sensitive to hydrolysis. The cleavage of the chlorosulphonyl group can, however, be accelerated by working-up the reaction mixture in the presence of an alkali metal bicarbonate such as sodium bicarbonate and an alkali metal sulphite such as sodium sulphite. This procedure is accordingly especially preferred. The above cycloaddition is preferably carried out in a temperature range of about —20° C. to about room temperature (about 20°-25° C.)

The S-oxidation of a compound of formula I in which n signifies the integer 0 can be carried out according to methods which are known per se and which are familiar to any person skilled in the art. A percarboxylic acid such as peracetic acid, m-chloroperbenzoic acid and the like is preferably used as the oxidation agent. Suitable solvents are, for example, halogenated hydrocarbons such as methylene chloride, chloroform and the like. The oxidation is conveniently carried out in a temperature range of about 0° C. to about room temperature.

The cleavage from a compound of formula I obtained of an acyl or tri(lower alkyl)silyl group which may be present can also be carried out according to methods which are known per se and which are familiar to any person skilled in the art. Tri(lower alkyl)silyl groups are preferably cleaved off by treatment with an aqueous mineral such as hydrochloric acid in a water-miscible organic solvent or solvent mixture. In a preferred embodiment there is used as the solvent a water-miscible cyclic ether such as tetrahydrofuran and a lower alcohol such as methanol. Acyl groups are preferably cleaved off by conventional mild basic hydrolysis.

The compounds of formula IIa which are used as starting materials can be prepared in accordance with the following Reaction Scheme:

Reaction Scheme

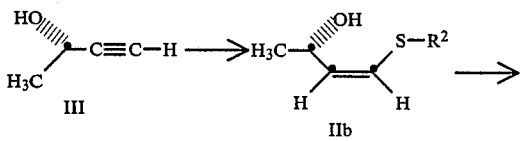

-continued
Reaction Scheme

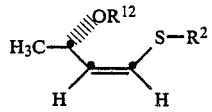

IIa in which $R^2$ and $R^{12}$ have the above significance.

A compound of formula IIb or a mixture thereof with the corresponding optical antipode can be prepared by reacting the compound of formula III or a mixture thereof with the corresponding optical antipode with a thiophenol which is substituted in the o- and/or the p-position by halogen, lower alkyl, lower alkylthio or lower alkoxy in the presence of a base. An alkali metal hydroxide such as potassium hydroxide is preferably used as the base. The reaction is preferably carried out in a temperature range of about 80° to about 120° C. and in the absence of a solvent.

The preparation of compounds of formula IIa from compounds of formula IIb can be carried out according to methods which are known per se and which are familiar to a person skilled in the art.

A compound of formula IIa in which $R^{12}$ signifies acyl can be prepared, for example, by acylating a compound of formula IIb with a corresponding acyl halide, preferably with a corresponding acyl chloride. Such an acylation is preferably carried out in an inert organic solvent, for example in a halogenated hydrocarbon such as methylene chloride, and in the presence of an acid-binding agent, for example an organic base such as pyridine, triethylamine and the like. The reaction is preferably carried out at a temperature in a range of about 0° C to about room temperature.

A compound of formula IIa in which $R^{12}$ signifies tri(lower alkyl)silyl is preferably prepared by reacting a compound of formula IIb with a tri(lower alkyl)-chlorosilane. Suitable solvents are, for example, halogenated hydrocarbons such as methylene chloride and N,N-dimethylformamide or mixtures thereof. The sylation is conveniently carried out in the presence of an organic base such as triethylamine and at room temperature.

A compound of formula IIa in which $R^{12}$ signifies a group of the formula —$BR^3R^4$ can be prepared, for example, by reacting a compound of formula IIb in an inert solvent with a borane of the general formula $HBR^3R^4$ in which $R^3$ and $R^4$ have the above significance. Suitable inert solvents are, for example, halogenated hydrocarbons such as methylene chloride and ethers such as diethyl eether. tetrahydrofuran and the like. This reaction is preferably carried out at about room temperature.

These compounds of formula IIa can, however. also be prepared by reacting a compound of formula IIb with a compound of the formula $ClBR^3R^4$ in which $R^3$ and $R^4$ have the above significance. Suitable solvents are, for example, halogenated hydrocarbons such as methylene chloride and ethers such as diethyl ether. This reaction is preferably carried out in a range of about 0° C. to about room temperature.

The compounds of formulae IIa and IIb are novel and are also objects of the present invention. The compounds of formula III as shown in the pictorial configuration or a mixture thereof with the corresponding optical antipode are known.

As mentioned above, the compounds of formula I can be used for the manufacture of antimicrobially active penems and carbapenems which have as a common structural element a (R)-1-hydroxyethyl group in the 6-position of the lactam ring. Compound I can be converted to such penems and carbapenems by conventional techniques.

In these penems and carbapenems, the asymmetrically substituted carbon atom of the hydroxyethyl group has the R-configuration, whereas the corresponding carbon atom in the compounds of formula I, namely the carbon atom denoted by α, has the S-configuration.

It is, however, readily possible to invert a compound of formula I in which $R^{11}$ signifies hydrogen and the carbon atom denoted by α has the S-configuration into a corresponding compound of formula I in which the carbon atom denoted by α has the R-configuration, i.e. into a compound of the formula

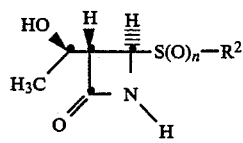

IV wherein n and $R^2$ have the above significance. Such an inversion can be carried out, for example, by treatment of compound I with formic acid in the presence of triphenylphosphine and diethyl azodicarboxylate, with an ether such as tetrahydrofuran being preferably used as the solvent. Such an inversion can, however, also be carried out readily at a later stage. The compounds of formula IV also are intermediates for producing the above mentioned penems and carbapenems.

The following Examples illustrate the present invention in more detail, but are not intended to limit its extent in any manner. All temperatures are given in degrees Celsius, and room temperature is about 20° to about 25° C. Unless indicated otherwise, percentages and ratios relating to solvent mixtures are expressed in volume and the remaining percentages and ratios are expressed in weight. Unless indicated otherwise, the Examples were carried out as written.

EXAMPLE 1

(a) A mixture of 4.5 g (31.1 mmol) of p-chlorothiophenol, 3.7 g (4.2 ml; 37.3 mmol) of 3-butyn-2-ol and 150 mg of powdered potassium hydroxide is heated to 100° C for 20 minutes. The brown crude product is then chromatographed on silica gel (ethyl acetate/hexane). There is obtained pure rac-(Z)-4-[(p-chlorophenyl)thio]-3-buten-2-ol.

(b) 1 g (4.6 mmol) of rac-(Z)-4-[(p-chlorophenyl)thio]-3-buten-2-ol in 50 ml of methylene chloride and 5 ml of N,N-dimethylformamide is treated at room temperature with 837 mg (5.5 mmol) of t-butyldimethylchlorosilane and 700 mg (0.9 ml; 69 mmol) of triethylamine, the reaction mixture is subsequently stirred for 5 hours and evaporated. The oil obtained is taken up in 200 ml of ether, washed three times with water and filtered through silica gel. There is obtained rac-(Z)-3-(t-butyldimethylsilyloxy)-1-butenyl-(p-chlorophenyl)sulphide.

(c) A solution of 4.65 g (14.35 mmol) of rac-(Z)-3-(t-butyldimethylsilyloxy)-1-butenyl-(p-chlorophenyl)sulphide in 50 ml of methylene chloride is cooled to −15° and treated with 3.05 g (1.9 ml; 21.5 mmol) of chlorosulphonyl isocyanate in 20 ml of methylene chloride (addition time about 15 minutes). The reaction mixture is subsequently stirred at -15° for 90 minutes and then evaporated carefully. A solution of the yellow oil obtained in 50 ml of dry ether is then slowly added dropwise to a mixture, cooled to 0°, of 60 ml of 5 percent sodium bicarbonate solution and 30 ml of 10 percent sodium sulphite solution (addition time about 10 minutes). The two-phase mixture is stirred vigorously for 2 hours, whereupon the aqueous phase is separated and extracted twice with 50 ml of ether each time. The combined organic phases are dried over sodium sulphate and evaporated. The oil obtained is chromatographed on silica gel with hexane/ethyl acetate (9:1). There is obtained a colourless oil which crystallizes slowly and which consists to about 83% of rac-(αS*,3S*,4R*)-3-[1-(t-butyldimethylsilyloxy)ethyl]-4-[(p-chlorophenyl)thio]-azetidinone; IR: 1760 cm$^{-1}$.

EXAMPLE 2

1.65 g (4.44 mmol) of ra -(αS*,3S*,4R*)-3-[1-(t-butyldimethylsilyloxy)ethyl]4-[(p-chlorophenyl)thio]-azetidinone are dissolved in 70 ml of tetrahydrofuran/methanol 12 percent hydrochloric acid (4:2:1). The solution is stirred at room temperature for 4 hours and then evaporated. The residue is taken up in 50 ml of ethyl acetate, washed with 20 ml of saturated sodium chloride solution and evaporated. The residue obtained is washed with ether/hexane (1:1) and dried. There is obtained pure rac-(αS*,3S*,4R*)-4-[(p-chlorophenyl)thio]-3-(1-hydroxyethyl)-2-azetidinone; IR: 1760 cm$^{-1}$.

EXAMPLE 3

617 mg (2.39 mmol) of rac-(αS*,3S*,4R*)-4-[(p-chlorophenyl)thio-3-(1-hydroxyethyl)-2-azetidinone in 30 ml of tetrahydrofuran are treated with 1.25 g (4.8 mmol) of triphenylphosphine and 0.18 ml (4.8 mmol) of formic acid. A solution of 1.1 g (4.8 mmol) of diethyl azodicarboxylate in 10 ml of tetrahydrofuran is slowly added dropwise thereto, the reaction mixture is stirred at room temperature for 2 hours, evaporated and the residue is filtered through silica gel (hexane/ethyl acetate). The oil obtained (680 mg) is dissolved in 30 ml of methanol, the solution is treated with 3 drops of concentrated hydrochloric acid, left to stand at room temperature for 2 hours and evaporated. The residue is filtered through silica gel (hexane/ethyl acetate). There is obtained rac--(αR*,3S*,4R*)-4-[(p-chlorophenyl)thio]-3-(1-hydroxyethyl)-2-azetidinone of melting point 130°; IR 1760 cm$^{-1}$.

EXAMPLE 4

(a) A mixture of 19.4 g (17 ml; 140 mmol) of thioanisole, 14.5 g (16.4 ml; 0.21 mmol) of 3-butyn-2-ol and 650 mg of powdered potassium hydroxide is heated to 100° for 15 minutes. The crude product obtained is chromatographed on silica gel. There is obtained pure rac-(Z)-4-[(p-methoxyphenyl)thio]-3-buten-2-ol.

(b) 14.1 g (67.1 mmol) of rac-(Z)-4-[(p-methoxyphenyl)thio]-3-buten-2-ol in 250 ml of of methylene chloride and 25 ml of N,N-dimethylformamide are treated with 15.2 g (100 mmol) of t-butyldimethylchlorosilane and 13.6 g (18.7 ml) of triethylamine, the reaction mixture is stirred at room temperature for 6 hours and evaporated. The oil obtained is taken up in 500 ml of ether, washed three times with 100 ml of water each time, dried over sodium sulphate and filtered through silica gel. There is obtained 4-[[(Z)-3-(t-butyldimethylsilyloxy)-1-butenyl]thio]anisole.

(c) A solution of 5.0 g (15.6 mmol) of 4-[[(Z)-3-(t-butyl-dimethylsilyloxy)-1-butenyl]thio]anisole in 50 ml of methylene chloride is cooled to −15° and treated slowly with 3.32 g (2.05 ml; 23.4 mmol) of chlorosulphonyl isocyanate in 20 ml of methylene chloride (addition time 15 minutes). The reaction mixture is stirred at −15° for 90 minutes and then evaporated carefully. The oil obtained is taken up in 50 ml of ether and slowly added dropwise to a mixture, cooled to 0°, of 30 ml of 5 percent sodium bicarbonate solution and 30 ml of 10 percent sodium sulphite solution. The two-phase mixture is stirred vigorously at 0° for 2 hours. The agueous phase is separated and ex tracted twice with 50 ml of ether each time. The combined organic phases are dried over sodium sulphate and evaporated. After chromatography on silica gel with ethyl acetate/hexane as the elution agent there is obtained an oil which crystallizes slowly and which consists of pure rac-(αS*,3S*,4R*) -3-[1-(t-butyldimethylsilyloxy)ethyl]-4-[(p-methoxyphenyl)thio]-2-azetidinone; IR 1760 cm⁻¹.

EXAMPLE 5

600 mg (1.68 mmol) of rac -(αS*,3S*,4R*)-3-[1-(t-butyldimethylsilyloxy)ethyl]-4-[(p-methoxyphenyl)thio]-2-azetidinone are dissolved in 35 ml of tetrahydrofuran/methanol/12 percent hydrochloric acid (4:2:1), whereupon the solution is stirred at room temperature for 4 hours and worked-up as described in Example 2. There is obtained rac-(αS*,3S*,4R*) -3-(1-hydroxyethyl)-4-[(p-methoxyphenyl)thio]-2-azetidinone as a colourless oil; IR: 1765 cm⁻¹.

EXAMPLE 6

2.04 g (11.43 mmol) of dicyclohexylborane are suspended in 40 ml of methylene chloride. The suspension is treated dropwise at room temperature with 2.4 g (11.43 mmol) of rac-(Z)-4 -[(p-methoxyphenyl)thio]-3-buten-2-ol in 15 ml of methylene chloride, stirred for a further 15 minutes, the solution obtained is cooled to 10°, 2.43 g (1.5 ml; 17.14 mmol) of chlorosulphonyl isocyanate are added dropwise thereto, the reaction mixture is stirred at −10° for a further 45 minutes and evaporated. The oil obtained is taken up in 50 ml of dry ether, the solution is added to a mixture, cooled to 0°, of 38 ml of 5 percent sodium bicarbonate solution, 28 ml of 10 percent sodium sulphite solution and 28 ml of water, stirred vigorously at 0° for 2 hours and the ethereal phase is separated. The aqueous phase is extracted twice with 50 ml of ethyl acetate each time. The organic phases are combined, dried over sodium sulphate and evaporated. The residue is chromatographed on silica gel (ethyl acetate/hexane). There is obtained a mixture of 2 diastereoisomeric racemates which contains about 60% of rac-(αS*, 3S*,4R*) -3-(1-hydroxyethyl)-4-[(p-methoxyphenyl)thio]-2-azetidinone; IR: 1760 cm⁻¹.

EXAMPLE 7

(a) 1 g (4.76 mmol) of rac-(Z)-4-[(p-methoxyphenyl)-thio]-3-buten-2-ol are dissolved in 50 ml of methylene chloride. whereupon the solution is treated with 0.77 ml (9.5 mmol) of pyridine and cooled to 0°. There is added dropwise thereto a solution of 0.5 ml (7.1 mmol) of acetyl chloride in 10 ml of methylene chloride and the mixture is stirred at 0° for 1 hour. The reaction mixture is washed successively with 50 ml of 1N hydrochloric acid, 50 ml of 5 percent sodium bicarbonate solution and 50 ml of saturated sodium chloride solution, dried over sodium sulphate and evaporated. By chromatography on silica gel with hexane/ethyl acetate (9:1) there is obtained pure rac-4-[[(Z)-3-acetoxy-1-butenyl]thio]anisole; IR: 1735 cm⁻¹.

(b) 1 g (3.96 mmol) of rac-4-[[(Z)-3-acetoxy-1-butenyl]thio]anisole are dissolved in 40 ml of methylene chloride, whereupon the solution is cooled to 0°, 0.52 ml (5.94 mmol) of chlorosulphonyl isocyanate is slowly added dropwise thereto and the reaction mixture is stirred at 0° for a further 2 hours. The mixture is evaporated, the residue is taken up in 50 ml of dry ether and the solution is added to a mixture, cooled to 0°, of 20 ml of 5 percent sodium bicarbonate solution and 15 ml of 10 percent sodium sulphite solution. After stirring vigorously for 1 hour the ethereal phase is separated, dried over sodium sulphate and evaporated. The crude product is chromatographed on silica gel. There is obtained a mixture of two diastereoisomeric racemates as an oil which contains about 75% of rac-(αS*,3S*,4R*)-3 -(1-acetoxyethyl)-4-[(p-methoxyphenyl)thio]-2-azetidinone; IR: 1740, 1760 cm⁻¹.

I claim:

1. A process for producing a compound of the formula:

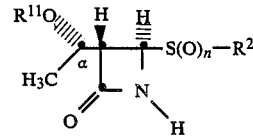

R¹¹ is hydrogen, lower alkanoyl or tri(lower alkyl)silyl, R² is phenyl which is subsituted in the o- and/or the p-position by halogen, lower alkyl, lower alkylthio or lower alkoxy and n is the integer 0 to 2, and mixtures thereof with the corresponding optical antipodes of the compound of formula I with the absolute configuration as depicted herein, which process comprises reacting a compound of the formula:

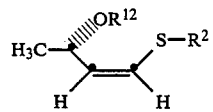

wherein R¹² is lower alkanoyl, tri(lower alkyl)silyl, or a group of the formula —BR³R⁴ and R³ and R⁴ have the same significance and each is a branched-open chain, cyclic or bicyclic hydrocarbon residue with 5-10 carbon atoms or together signify an open chain or cyclic hydrocarbon residue with 5-10 carbon atoms and two free valences and R² has the above significance, or a mixture thereof including the corresponding optical antipode, with chlorosulphonyl isocyanate to obtain a compound of formula I.

2. The process of claim 1, further comprising S-oxidizing the resulting compound of formula I in which n is the integer 0 and, cleaving off an lower alkanoyl or tri(lower alkyl)silyl group which may be present.

3. The process of claim 1, further comprising carrying out the reaction of the compound of formula IIa with chlorosulphonyl isocyanate in a halogenated hydrocarbon as a solvent.

4. The process of claim 1, wherein the halogenated hydrocarbon is methylene chloride.

5. The process of claim 1, wherein the reaction mixture obtained after the reaction of the compound of formula IIa with chlorosulphonyl isocyanate is worked-up in the presence of an alkali metal bicarbonate and an alkali metal sulphite.

* * * * *